Feb. 25, 1941. W. E. LAMMERTS Plant Pat. 454
ROSE PLANT
Filed Oct. 14, 1940
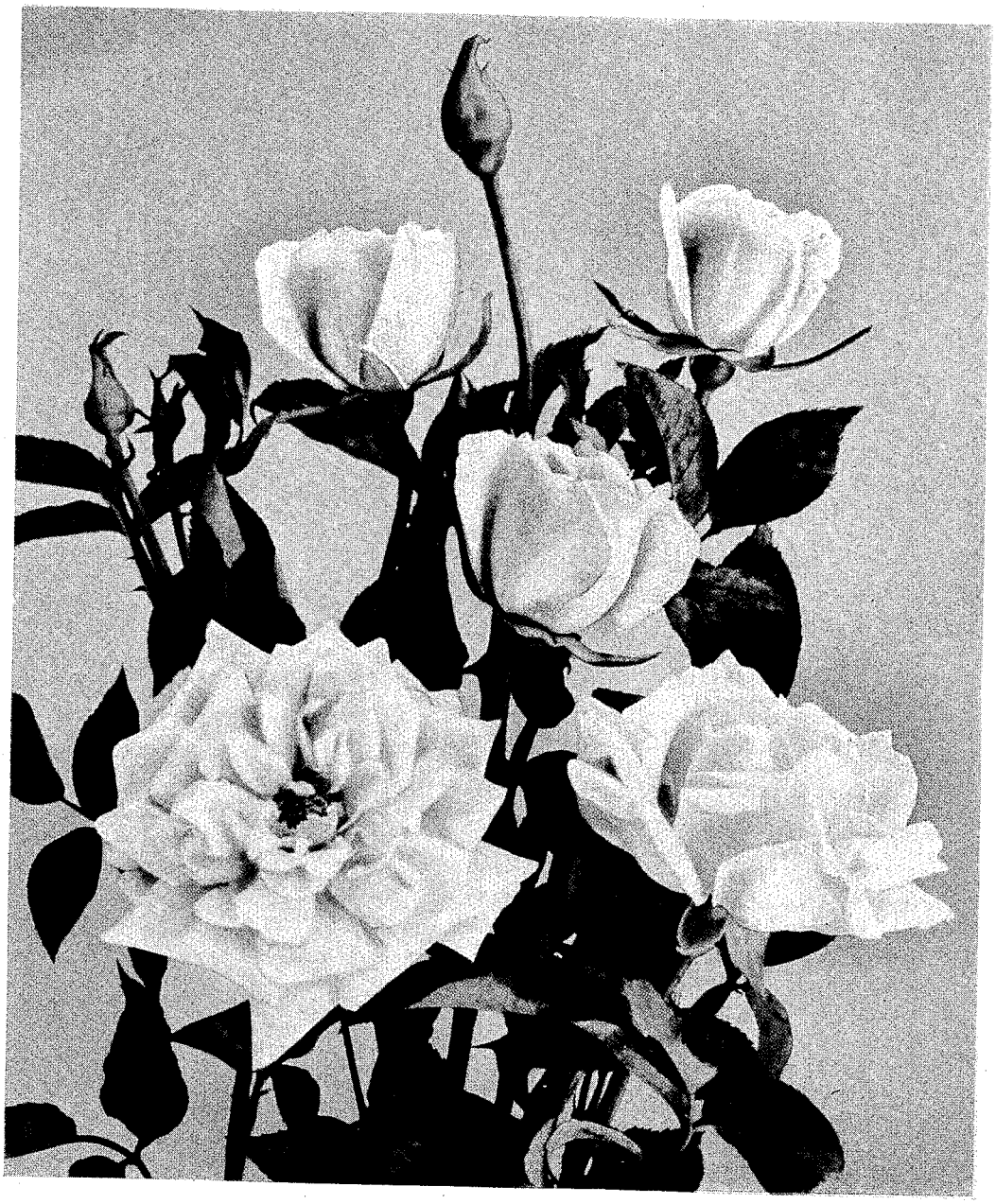
Inventor
W. E. Lammerts
By Robbins & Robb
Attorneys Patented Feb. 25, 1941

Plant Pat. 454

UNITED STATES PATENT OFFICE

454

ROSE PLANT

Walter E. Lammerts, Ontario, Calif., assignor to Armstrong Nurseries, Ontario, Calif., a corporation of California Application October 14, 1940, Serial No. 361,190

1 Claim. (Cl. 47—61)

The present invention relates to a new and distinct variety of rose plant of the hybrid tea class, originating as a cross between "Lulu" and "Mrs. Sam McGredy" varieties and inheriting most of the good qualities of each, in that the glossy foliage and unusual color resembles that of Mrs. Sam McGredy while the shape of the bud and the floriferousness takes after Lulu.

The primary distinguishing features of the new rose may be summarized as follows:

The extremely bushy habit of growth of the plant to medium height clothed with small to medium-sized glossy foliage which is highly resistant to mildew; the extreme floriferousness; the unusual colorings of the flowers in orange, salmon, buff and pink tones; the small to medium-sized urn-shaped buds of an appropriate size for use as a boutonniere or outdoor-grown corsage; the pleasant tea fragrance of moderate intensity; and the long-lasting quality of the buds which contain approximately fifty petals.

The following is a detailed description of this new rose, the color terminology employed therein being in accord with Ridgway's Color Standard.

Type: Tender; tall; bush; outdoor; seedling; for cut flowers and garden decoration.
Class: Hybrid tea.
Parentage:
*Seed parent.*—Lulu.
*Pollen parent.*—Mrs. Sam McGredy.
Propagation: It holds its distinguishing characteristics through succeeding propagations by budding.

*Flower*

Locality where grown: Ontario, California.
Flowers borne: Singly to several to stem; in irregular cluster; on normal, medium long stems.
Quantity of bloom: Abundant, outdoors.
Continuity: Continuous through rose season.
Fragrance: Moderate; spicy.
Bud:

*Peduncle.*—Medium to long; slender; erect; medium rough; few to numerous gland-tipped cilia, with near Bordeaux, Plate XII, tips. Peduncle near Mignonette Green, Plate XXXI, blotched irregularly with near Garnet Brown, Plate I.

*Before calyx breaks.—Size*—small. *Form*—Long, pointed, with foliaceous appendages and gland-tipped cilia on the surface of the bud; with slender foliaceous parts extending beyond the tip of the bud equal to one-half or more of its length.

*As calyx breaks.*—Begonia Rose, Plate I, to near Strawberry Pink, Plate I. Inner surface with fine, woolly tomentum; margins exposed before calyx breaks lined with gland-tipped cilia and foliaceous appendages. Margins not exposed before calyx breaks lined with fine tomentum.

*As first petal opens.—Size*—small to medium. *Form*—ovid to urn-shaped. *Color:* outside—Grenadine Pink, Plate II, to near Bittersweet Orange, Plate II, to near Empire Yellow, Plate IV, on small area at base; inside—Capucine-Buff, Plate III, at tip, Capucine Orange, Plate III, along sides, Capucine Yellow, Plate III, near base; veining near Cadmium Yellow, Plate III; small area near Lemon Chrome, Plate IV, at base. *Opening*—opens up well.

Bloom:
*Size, when fully open.*—Small to medium, 2¾ inches to 3½ inches.
*Petalage.*—Double to very double; from forty to fifty petals.
*Form.*—High center at first, remaining high centered; petals at first tightly rolled outwardly; becoming later, at maturity, loosely rolled.

Petals: Thick; soft; with inside velvety and outside satiny.
*Shape.*— Outside— Obovate, entire. Intermediate—obovate, entire. Inside—oblanceolate-lanceolate, entire or with pointed apex.

*Color.*—Tinted with other colors.

This description of a newly opened flower was made from a rose grown outdoors in September, 1940, at Ontario, California:
*Color.*—Outside petal: outside surface—near Grenadine Pink, Plate II, small area at base near Empire Yellow, Plate IV; inside surface—near Orange Pink, Plate II, at tip, near Salmon, Plate XIV, along sides with near Cadmium Yellow, Plate III, in veinings. Small area at base near Lemon Chrome, Plate IV. Intermediate petals: outside surface—near Rose Doree, Plate I, with frequently a stripe from $\frac{1}{32}''$ to $\frac{1}{16}''$ wide over and about area of midrib near Light Green Yellow, Plate V, in color. Very small area at base near Empire Yellow, Plate IV; inside surface—near Salmon Color, Plate XIV, at tip, between Capucine Orange, Plate III, and Capucine Yellow, Plate III, near center with small area at base near Lemon Chrome, Plate IV. Inner petal: outside surface—Grenadine Pink, Plate II, with occasional small stripes radiating from base Light Green Yellow, Plate V, in color; inside surface—near Capucine Orange, Plate III, with area at base near Lemon Chrome, Plate IV.

This description was made from a rose that was open for three days outdoors in September, 1940, at Ontario, California:

*Color.*—Outside petal: outside surface—near Rose Pink, Plate XII, at extreme tip, Pale Salmon Color, Plate XIV, to Salmon-Buff, Plate XIV, near center; near Orange-Buff; Plate III, toward base with Light Greenish Yellow, Plate V, at extreme base; inside surface—near Pale Ochraceous Salmon, Plate XV, at tip to near Orange-Buff, Plate III, near center to near Strontian Yellow, Plate XVI, on small area at base. Veinings Capucine Yellow, Plate III, influencing general color effect of individual petal. Inside petal: outside surface—near Jasper Pink, Plate XIII, at tip to near Orange Pink, Plate II, near center. Base near Pale Greenish Yellow, Plate V; inside surface—tip near Pale Flesh Color, Plate XIV, center near Salmon-Buff, Plate XIV, base near Strontian Yellow, Plate XVI.

*General color effect.*—Newly opened flower—Carrot Red, Plate XIV, to Apricot Buff, Plate XIV. Three days open—near Flesh Color, Plate XIV.

*Behavior.*—Persist; fading near White, Plate LIII, at tips of petals to near Cartridge-Buff, Plate XXX, at base of petals just before flowers wither. Affected by hot, dry weather as follows: Slightly more Pink on outside of petals.

*Flower longevity.*—On bush in garden four days in September; cut roses grown outdoors kept at living-room temperatures six days in September.

*Reproductive organs*

Stamens: Few; arranged irregularly about pistils, mixed with petaloids.

Filaments: Short; Yellow; most with anthers, near Lemon Yellow, Plate IV, in color.

Anthers: Medium size; open at various times; near Deep Chrome, Plate III, when young with near Peach Red, Plate I, to near Brazil Red, Plate I, markings as pollen escapes.

Pollen: Sparse; near Cadmium Yellow, Plate III.

Pistils: Many.

Styles: Uneven; medium long; slender; bunched; Color on most near Pomegranate Purple, Plate XII, some with near Spectrum Red, Plate I, near stigma to near Pale Orange Yellow, Plate III, at base.

Stigma: Near Apricot-Buff, Plate XIV.

Ovaries: All enclosed in calyx.

Hips: Short; globular with inconspicuous neck; smooth and rough; walls thick, fleshy; near Scheele's Green, Plate VI, when half mature, becoming near Lime Green, Plate XXXI, as it approaches maturity.

Sepals: Permanent; moderately long; straight; spear-shaped; recurved.

*Color.*—Inside—near Corydalis Green, Plate XLI. Outside—near Biscay Green, Plate XVII, occasionally blotched with near Pansy Purple, Plate XII.

Seeds: Few; medium size.

*Plant*

Foliage:

*Leaves.*—Compound of three to five leaflets; moderately abundant; medium size; moderately heavy, leathery, glossy.

*Leaflets.*—Ovate; lanceolate, with apex acute; base round; margin doubly serrate,

*Color.*—*Mature:* Upper surface—near Dark Dull Yellow Green, Plate XXXII; under surface—near Light Elm Green, Plate XVII. *Young:* Upper surface—near Dark Perilla Purple, Plate XXXVII, laid over indistinct shade of green; under surface—near Neutral Red, Plate XXXVIII.

*Rachis* (the supporting stem of the compound leaf).—Medium heavy. Upper side—grooved, hairy, glandular. Under side—sparsely prickly, glandular.

*Stipules.*—Medium long; narrow; with medium long points, turning out at an angle of less than 45°, recurved toward the stem.

*Disease.*—Resistant to mildew.

Growth: Dwarf; bushy; spreading; much branched.

*Growth.*—Vigorous.

*Canes.*—Medium heavy.

*Main stems.*—Near Jade Green, Plate XXXI; as bark becomes older dotted and lined irregularly with slightly raised corky portions formed by splitting bark. *Large prickles*—many; medium long; hooked downward, with long, narrow base; near Hessian Brown, Plate XIII, with occasional markings of slightly lighter color. *Small prickles*—few; near Hessian Brown, Plate XIII, with occasional markings of slightly lighter color. *Hairs*—none.

*Branches.*—Near Parrot Green, Plate VI. *Large prickles*—many; medium long; hooked downward; with long, narrow base; from Honey Yellow, Plate XXX, to near Tawny, Plate XV. *Small prickles*—few; from Honey Yellow, Plate XXX, to near Tawny, Plate XV. *Hairs*—none.

*New shoots.*—Near Madder Brown, Plate XIII, on portions most exposed to sun to near Grape Green, Plate XLI, on portions unexposed. *Large prickles*—many; medium long; hooked downward; with long, narrow base; from near Garnet Brown, Plate I, at base to near Grape Green, Plate XLI, at tip. *Small prickles*—few; from near Garnet Brown, Plate I, at base to near Grape Green, Plate XLI, at tip. *Hairs*—none.

I claim:

A new and distinct variety of hybrid tea rose plant, characterized as to novelty by its bushy habit of growth with glossy foliage highly resistant to mildew; extreme floriferousness; unusual coloring of the flowers; size and shape of the buds; moderate and pleasant fragrance, and the long-lasting quality of the buds which contain numerous petals, substantially as shown and described.

WALTER E. LAMMERTS.